(12) United States Patent  (10) Patent No.: US 8,158,808 B2
Winter  (45) Date of Patent: Apr. 17, 2012

(54) SYNTHESIS AND PREPARATIONS OF DULOXETINE SALTS

(75) Inventor: Stephen Benedict David Winter, Barcelona (ES)

(73) Assignee: Medichem S.A., Barcelona (ES)

( * ) Notice: Subject to any disclaimer, the term of this patent is extended or adjusted under 35 U.S.C. 154(b) by 0 days.

(21) Appl. No.: 12/762,131

(22) Filed: Apr. 16, 2010

(65) Prior Publication Data

US 2010/0286412 A1 Nov. 11, 2010

Related U.S. Application Data

(62) Division of application No. 12/097,251, filed as application No. PCT/IB2006/004194 on Dec. 12, 2006, now abandoned.

(60) Provisional application No. 60/749,095, filed on Dec. 12, 2005, provisional application No. 60/749,096, filed on Dec. 12, 2005, provisional application No. 60/749,097, filed on Dec. 12, 2005, provisional application No. 60/815,835, filed on Jun. 23, 2006, provisional application No. 60/815,854, filed on Jun. 23, 2006, provisional application No. 60/815,856, filed on Jun. 23, 2006.

(30) Foreign Application Priority Data

Dec. 12, 2006 (WO) ................ PCT/IB2006/004250
Dec. 12, 2006 (WO) ................ PCT/IB2006/004252

(51) Int. Cl.
*C07D 333/16* (2006.01)
(52) U.S. Cl. ........................................ 549/72
(58) Field of Classification Search .............. 549/72
See application file for complete search history.

(56) References Cited

FOREIGN PATENT DOCUMENTS

CA  2 634 008  10/2007
CA  2 634 009  10/2007

OTHER PUBLICATIONS

Olofson, R., "New, useful reactions of novel haloformates and related reagents", Pure & Appl. Chem., vol. 80, No. 11, pp. 1715-1724, 1988.

*Primary Examiner* — Taofiq A Solola
(74) *Attorney, Agent, or Firm* — Cozen O'Connor

(57) ABSTRACT

The invention relates to an improved process for the preparation of duloxetine, duloxetine intermediates, and duloxetine hydrochloride.

17 Claims, 9 Drawing Sheets

SYNTHESIS AND PREPARATIONS OF DULOXETINE SALTS

CROSS REFERENCE TO RELATED APPLICATIONS

This application is a divisional of U.S. application Ser. No. 12/097,251, filed Sep. 30, 2008, now abandoned, which claims priority under 35 U.S.C. §371 to International Patent Application No. PCT/IB2006/004194 (filed Dec. 12, 2006), which claims priority to U.S. Provisional Application Nos. 60/749,095, 60/749,096, and 60/749,097 (filed Dec. 12, 2005) and 60/815,835, 60/815,854, and 60/815,856 (filed Jun. 23, 2006), as well as to International Patent Applications Nos. PCT/IB2006/004252 and PCT/IB2006/004250 (filed Dec. 12, 2006), all of which applications are expressly incorporated herein by reference in their entirety.

BACKGROUND OF THE INVENTION

1. Field of the Invention

The invention relates to an improved process for the preparation of duloxetine, duloxetine intermediates, and duloxetine hydrochloride.

2. Discussion of the Related Art

Duloxetine hydrochloride (Compound I) is the international commonly accepted name for N-methyl-N-[(3S)-(3-(1-naphthyloxy)-3-thien-2-yl)propyl]amine hydrochloride (which is also known as methyl-[(S)-3-(naphthalen-1-yloxy)-3-thiophen-2-yl-propyl]-amine) hydrochloride and has an empirical formula of $C_{18}H_{19}NOS \cdot HCl$ and a molecular weight of 333.88. Duloxetine hydrochloride is a commercially marketed pharmaceutically active substance known to be useful for the treatment of major depressive disorder.

Duloxetine hydrochloride is a selective serotonin and norepinephrine reuptake inhibitor (SSNRI) for oral administration. In the United States, duloxetine hydrochloride is marketed under the name Cymbalta® for the treatment of major depressive disorder and diabetic peripheral neuropathic pain. In Europe, duloxetine hydrochloride has been approved for the treatment of major depressive disorder and also for the treatment of moderate to severe stress urinary incontinence.

Duloxetine and its pharmaceutically acceptable salts are disclosed in U.S. Pat. No. 5,023,269 ("the '269 patent"). No examples related to the preparation of (S)-duloxetine, or one of its pharmaceutically acceptable salts (e.g., the hydrochloride salt), are disclosed. In the '269 patent, racemic duloxetine was prepared by demethylating the corresponding N,N-dimethylpropanamine derivative using phenyl chloroformate to yield the corresponding carbamate as an intermediate. The carbamate was then hydrolyzed to afford racemic duloxetine as an oil, and was subsequently isolated as the oxalate salt. The process disclosed in the '269 patent for obtaining racemic duloxetine is shown in Scheme 1.

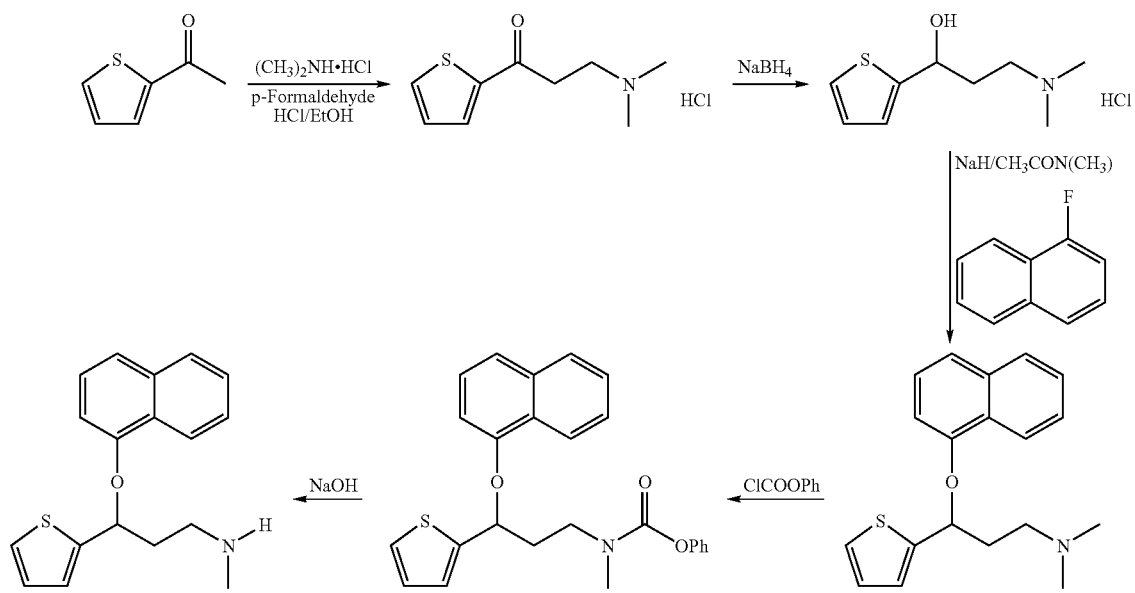

(S)-Duloxetine can be obtained using the same strategy outlined in Scheme 1, but starting from (S)-3-dimethylamino-1-(2-thienyl)-1-propanol (Compound S-II), as described in *Tetrahedron Letters*, 31, (49), 7101-04 (1990) and in U.S. Pat. No. 5,362,886 ("the '886 patent"). The '886 patent also provides a procedure for the preparation of (S)-duloxetine in the form of its hydrochloride salt.

Compound S-II

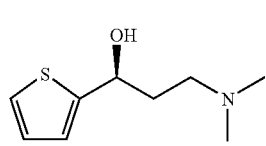

Other references related to the preparation of duloxetine hydrochloride from compound of formula S-II are WO 04/056795, WO 03/062219 and WO 00/61540.

There are several other known methods for producing duloxetine and its salts. Generally, these alternative processes include resolution of a key intermediate or a stereoselective synthesis usually involving a stereospecific reduction of a keto group to give the corresponding alcohol. These other processes include those disclosed in: WO 03/070720; WO 04/011452; WO 04/024708; *T. Chirality*, 12:26-29 (2000); *Advanced Synthesis and Catalysis* (2003), 345(1+2), 261-274; WO 04/005307; JP 2004123596; WO 04/13123; WO 04/005220; and *Tetrahedron: Asymmetry* (2003), 14(12), 1631-1636.

In patent application WO 04/056795 duloxetine hydrochloride is prepared by using a phase transfer catalyst for the reaction of (S)-3-(dimethylamino)-1-(2-thienyl)-1-propanol (Compound S-II) and 1-fluoronaphthalene (Scheme I, Compound III) with sodium hydroxide in DMSO.

SUMMARY OF THE INVENTION

The invention relates to an improved process for the preparation of duloxetine hydrochloride.

In particular, the invention provides an improved process for the preparation of duloxetine hydrochloride as shown, generally, in Scheme 2 (below).

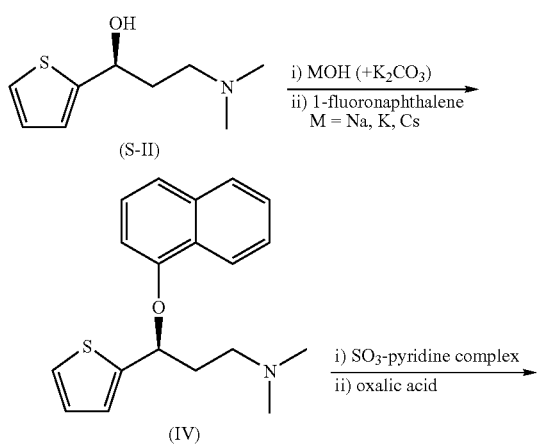

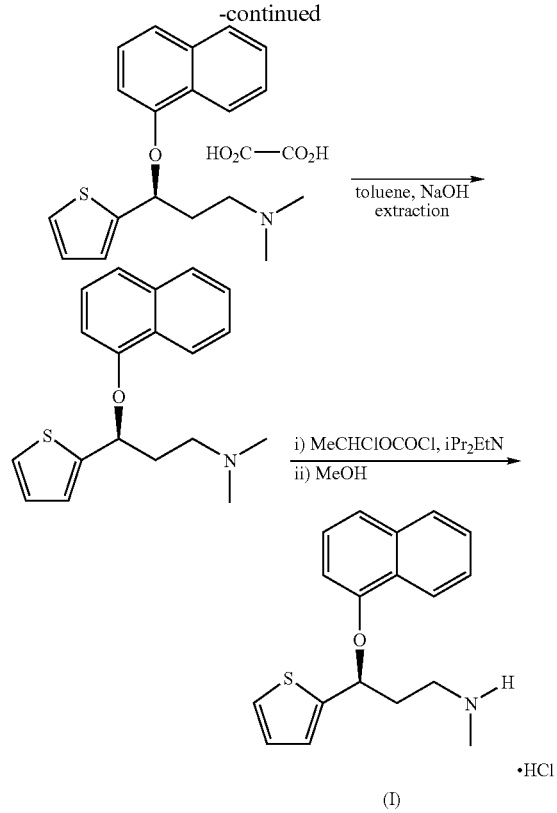

In this process, a phase transfer catalyst is not required and good yields of (S)-N,N-dimethyl-gamma-(1-naphthyloxy)-2-thiophenepropylamine (Compound IV) may be obtained with the enantiomeric excess substantially retained. Additionally, according to this process, Compound IV can be selectively purified from unreacted starting materials.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE PREFERRED EMBODIMENTS

Figure 1:
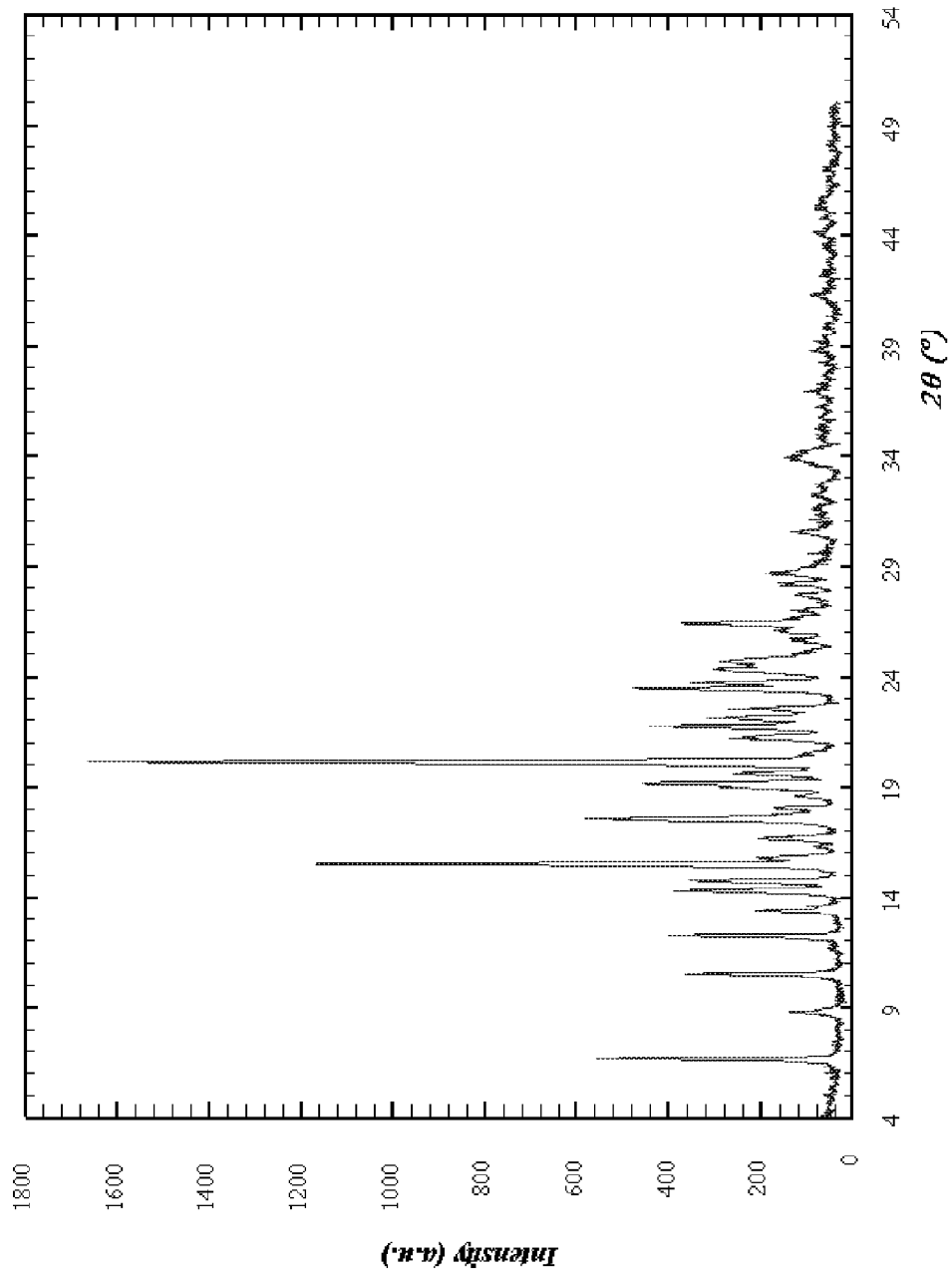
FIG. 1 illustrates the X-ray powder diffractogram (XRD) of (S)-N,N-dimethyl-(3-(1-naphthyloxy)-3-thien-2-yl)propylamine oxalic acid salt, Form A, obtained in Example 10.

Reference will now be made in detail to the preferred embodiments of the invention. This invention may, however, be embodied in many different forms and should not be construed as limited to the embodiments set forth herein. In addition, and as will be appreciated by one of skill in the art, the invention may be embodied as a method, system or process.

The invention relates to an improved process for the preparation of duloxetine hydrochloride.

In particular, one aspect of the invention includes a method for preparing duloxetine and duloxetine intermediates from (S)-3-(dimethylamino)-1-(2-thienyl)-1-propanol (Compound S-II) and 1-fluoronaphthalene (Compound III) using an alkaline metal hydroxide or alkoxide, in DMSO or DMSO-cosolvent mixtures, in the absence of a phase transfer catalyst and with a low degree of the undesired racemization. This process can that optionally include using potassium carbonate or sodium sulphate. The alkaline metal hydroxide or alkoxide used can be, for example, NaOH, KOH or CsOH.

Another aspect of the invention includes the method described above, further characterized by a product in which the enantiomeric purity is >94:6 ratio of enantiomers.

Another aspect of the invention includes the method described above further including the step of partially distilling the solvent and thereby removing water from the reaction mixture and increasing the rate of reaction.

Another aspect of the invention includes a method for purifying (S)-N,N-dimethyl-3-(1-naphthalenyloxy)-3-(2-thienyl)-1-propylamine (Compound IV, which is also known as dimethyl-[(S)-3-(naphthalen-1-yloxy)-3-thiophen-2-yl-propyl]-amine), which is a duloxetine intermediate, in which Compound IV is selectively purified from (S)-3-(dimethylamino)-1-(2-thienyl)-1-propanol (Compound S-II) by means of forming a derivative of (S)-3-(dimethylamino)-1-(2-thienyl)-1-propanol (Compound S-II) in a solvent. Preferably the derivative is an ester derivative including, more preferably, a mineral acid ester derivative.

Another aspect of the invention includes the method for purifying (S)-N,N-dimethyl-3-(1-naphthalenyloxy)-3-(2-thienyl)-1-propylamine described above further including the use of pyridine sulfur trioxide to form a sulphate derivative of (S)-3-dimethylamino-1-(2-thienyl)-1-propanol; Compound S-II).

Another aspect of the invention includes the methods for purifying (S)-N,N-dimethyl-3-(1-naphthalenyloxy)-3-(2-thienyl)-1-propylamine described above wherein the solvent used is at least one of a hydrocarbon solvent, an ester solvent, an ether solvent or combinations thereof. Preferred hydrocarbon solvents include heptane and toluene, where toluene is more preferred. Preferred ester solvents include ethyl acetate, isopropyl acetate and isobutyl acetate are preferred, where ethyl acetate or isopropyl acetate are more preferred. Preferred ether solvents include tertbutyl methyl ether and tetrahydrofuran.

Another aspect of the invention includes a method for demethylating (S)-N,N-dimethyl-3-(1-naphthalenyloxy)-3-(2-thienyl)-1-propylamine (Compound IV) that includes reacting Compound IV with a chloroformate, preferably where the chloroformate is 1-chloroethyl chloroformate, in the presence of an acid scavenger in a solvent. The amount of acid scavenger is preferably from approximately 0.02 to approximately 2 equivalents relative to Compound IV, more preferably from approximately 0.05 to approximately 1 equivalents relative to Compound IV and most preferably approximately 0.1 equivalents relative to Compound IV.

Another aspect of the invention includes a method for demethylating (S)-N,N-dimethyl-3-(1-naphthalenyloxy)-3-(2-thienyl)-1-propylamine (Compound IV) as described above wherein the acid scavenger is a hindered tertiary amine.

Another aspect of the invention includes a method for demethylating (S)-N,N-dimethyl-3-(1-naphthalenyloxy)-3-(2-thienyl)-1-propylamine (Compound IV) as described above wherein the acid scavenger is diisopropylethylamine.

The solvent used for the demethylation reaction is preferably at least one of an aromatic solvent, an ester solvent, an ether solvent or combinations thereof. Preferred aromatic solvents include toluene and xylene, where toluene is more preferred. Preferred ester solvents include ethyl acetate, isopropyl acetate and isobutyl acetate, where ethyl acetate or isopropyl acetate are more preferred. Preferred ether solvents include tertbutyl methyl ether and tetrahydrofuran.

Another aspect of the invention includes a method for the demethylation of (S)-N,N-dimethyl-3-(1-naphthalenyloxy)-3-(2-thienyl)-1-propylamine (Compound IV) as described above further including a treatment step with an alcohol, a ketone, an ether, water or mixtures thereof at a temperature of less than or equal to 50° C., preferably of less than or equal to 40° C.

The invention further includes a method for synthesizing (S)-N-methyl-[3-(naphthalen-1-yloxy)-3-thiophen-2-yl-propyl]-carbamic acid 1-chloroethyl ester including reacting (S)-N,N-dimethyl-3-(1-naphthalenyloxy)-3-(2-thienyl)-1-propylamine (Compound IV) with 1-chloroethyl chloroformate in the presence of an acid scavenger.

Another aspect of the invention includes a method for synthesizing (S)-N-methyl-[3-(naphthalen-1-yloxy)-3-thiophen-2-yl-propyl]-carbamic acid 1-chloroethyl ester as described above wherein the acid scavenger is a hindered tertiary amine.

Another aspect of the invention includes a method for synthesizing (S)-N-methyl-[3-(naphthalen-1-yloxy)-3-thiophen-2-yl-propyl]-carbamic acid 1-chloroethyl ester as described above wherein the acid scavenger is diisopropylethylamine.

It will be apparent to those skilled in the art that various modifications and variations can be made in the present invention and specific examples provided herein without departing from the spirit or scope of the invention. Thus, it is intended that the present invention covers the modifications and variations of this invention that come within the scope of any claims and their equivalents.

SPECIFIC EXAMPLES

The following examples are for illustrative purposes only and are not intended, nor should they be interpreted to, limit the scope of the invention.

General Experimental Conditions:

I. HPLC Method a. Chromatographic Purity HPLC Method

Chromatographic separation was carried out in a Phenomenex Luna C18, 5 µm, 4.6×150 mm column at room temperature (20-25° C.).

The mobile phase was prepared by mixing 500 mL of acetonitrile with 500 mL buffer (pH=2), which was prepared from 18.40 g of hexafluorophosphate dissolved in 1000 mL of water. The pH was adjusted to 2 with phosphoric acid. The mobile phase was mixed and filtered through a 0.22 µm nylon membrane under vacuum.

The chromatograph was equipped with a 220 nm detector, and the flow rate was 1 mL per minute. Test samples (10 µL) were prepared by dissolving an appropriate amount of sample in the mobile phase in order to obtain 0.5 mg of sample per mL. The chromatogram was run for at least 30 minutes.

b. HPLC Chiral Method

The chromatographic separation was carried out in a Daicel CHIRALCEL OD-RH, 5 µm, 4.6×150 mm column at room temperature (20-25° C.).

The mobile phase was prepared by mixing 600 mL of acetonitrile with 400 mL of buffer (pH=2) which was prepared from 18.40 g of hexafluorophosphate dissolved in 1000 mL of water. The pH was adjusted to 2 with phosphoric acid. The mobile phase was mixed and filtered through a 0.22 µm nylon membrane under vacuum.

The chromatograph was equipped with a 216 nm detector and the flow rate was 0.5 mL per minute. Test samples (5 µL) were prepared by dissolving the appropriate amount of sample in the mobile phase in order to obtain 0.5 mg of sample per mL. The chromatogram was run for at least 25 minutes.

Example 1

Preparation of (S)-N,N-dimethyl-(3-(1-naphthyloxy)-3-thien-2 yl) propylamine oxalic acid salt (S)-3-Dimethylamino-1-(2-thienyl)-1-propanol (50 g, 0.270 moles) and sodium hydroxide (21.6 g, 0.540 moles, 2 eq.) were heated in DMSO (500 mL) at 60-80° C. for 1 hour. The temperature was controlled at 60° C.±4° C. before 1-fluoronaphthalene (43.6 g, 38.5 mL, 0.299 moles) was added. The mixture heated at this temperature for 64 hours. Water (500 mL) was added, and the mixture extracted with toluene (2×500 mL). The organic layers were then combined and washed with water (500 mL). HPLC analysis of an evaporated aliquot showed the molar ratio of Compound IV to Compound S-II to be 90:10 and Compound IV to be 88% ee. Pyridine sulfur trioxide (6.4 g, 0.040 moles) was added to the mixture, the mixture was stirred for 30 minutes, and was then washed with water (500 mL). The organic layers were then concentrated by distillation until 600 mL of solvent was removed, and ethyl acetate (500 mL) was added. Oxalic acid dihydrate (27.2 g, 0.216 moles) was then added. The resulting suspension was stirred for 16 hours and filtered to yield the product as a white solid. The resulting product was slurried in additional ethyl acetate (200 mL), filtered and dried under vacuum to yield 63.3 g of the product as a white solid (0.158 moles, Yield: 59%). The resulting product had a molar ratio of Product:(S)-3-dimethylamino-1-(2-thienyl)-1-propanol:1-fluoronaphthalene of 99.53:0.46:0.02 and 88% ee.

Example 2

Preparation of (S)-N-Methyl-[3-(naphthalen-1-yloxy)-3-thiophen-2-yl-propyl]-carbamic acid phenyl ester (S)-N,N-Dimethyl-(3-(1-naphthyloxy)-3-thien-2-yl)propylamine (46.5 g) was dissolved in toluene (500 mL) and diisopropylethylamine (30.7 mL) was added followed by phenyl chloroformate (28.1 mL). The mixture was then heated to 60° C. for 3 hours, and additional phenyl chloroformate (5 mL) and diisopropylethylamine (7 mL) was added. The mixture was then stirred at 60° C. for an additional 6 hours, cooled to ambient temperature, and washed with 4% NaHCO$_3$ solution (400 mL). The layers were then separated, and the aqueous phase was extracted with toluene (2×200 mL). The three organic layers were then combined, washed with water (300 mL), and concentrated to yield (S)-N-Methyl-[3-(naphthalen-1-yloxy)-3-thiophen-2-yl-propyl]-carbamic acid phenyl ester as an oil (64.55 g).

Example 3

Preparation of (S)-N-methyl-(3-(1-naphthyloxy)-3-thien-2-yl) propylamine (Duloxetine Base)

Sodium hydroxide (19 g) and water (25 mL) were added to a solution of (S)-N-Methyl-[3-(naphthalen-1-yloxy)-3-thiophen-2-yl-propyl]-carbamic acid phenyl ester (64.8 g) dissolved in DMSO (250 mL). The mixture was heated at 115° C. for 6 hours, cooled to ambient temperature, and water (200 mL) was added. The mixture was then extracted with toluene (2×200 mL) and the organic layers were combined. The organic layers were then washed with brine (100 mL), dried over sodium sulfate, filtered and concentrated. The resulting residue was then dissolved in methanol (500 mL), combined with activated carbon (2 g), and heated at reflux for 1 hour. After cooling, the mixture was filtered through Celite® (20 g), the filter cake was washed with methanol (50 mL), and the solution was concentrated to yield duloxetine base as an oil (37.07 g, Yield: 92% yield, Chiral HPLC: 90% ee).

Example 4

Preparation of (S)-N-methyl-(3-(1-naphthyloxy)-3-thien-2-yl) propylamine hydrochloride (Duloxetine hydrochloride) from Duloxetine base Duloxetine base (99% ee, 0.5 g, 1.68 mmoles) was dissolved in acetone (5 mL) and stirred with cooling in an ice-water bath. Hydrochloric acid in diethyl ether (2M, 0.8 mL) was added, and a precipitate formed within 2 minutes. The mixture was stirred at ambient temperature 16 hours, filtered and the collected solid washed with acetone (0.5 mL). The white solid was then dried under vacuum at ambient temperature to yield duloxetine hydrochloride (0.485 g, 1.45 mmoles, yield: 86%; Chiral HPLC: 99.5% ee).

Example 5

Preparation of (S)-N-methyl-(3-(1-naphthyloxy)-3-thien-2-yl) propylamine hydrochloride (Duloxetine hydrochloride)

Sodium tert-pentoxide (1.06 kg of a 40% solution in toluene, 3.85 moles, 0.95 eq.) was added over 10 minutes to a suspension of (S)-3-dimethylamino-1-(2-thienyl)-1-propanol (750 g, 4.05 moles) dissolved in DMSO (3 L) at a temperature of 13-15° C. The (S)-3-dimethylamino-1-(2-thienyl)-1-propanol was dissolved completely to form a brown solution. The mixture was then heated to 70° C. for one hour before 1-fluoronaphthalene (710 g, 4.86 moles) was added over 5 minutes. The mixture was then heated at 70° C. for 7 hours. The molar ratio of product (Compound IV) to starting alcohol (Compound S-II) was observed to be 91.6:8.4 as determined by HPLC of an aliquot. The mixture was next cooled to 20° C., quenched with water (5 L), and extracted twice with isopropyl acetate (4+3 L). The organic layers were then combined, washed with water (4 L), and pyridine sulphur trioxide complex (64 g, 0.4 moles, 0.1 eq.) was added. The mixture was stirred at 20° C. for 30 minutes, and washed with water (5 L). Oxalic acid dihydrate (0.41 kg, 3.2 moles, 0.8 eq.) was then added, and the mixture was stirred at 25° C. for 2.5 hours and then at 20° C. for 2 days. The mixture was next filtered and washed with isopropyl acetate (2.5 L) to yield (S)-N,N-dimethyl-(3-(1-naphthyloxy)-3-thien-2-yl) propylamine oxalic acid salt as an off-white solid (2.3 kg (wet product), equivalent to 1.3 kg (dry product) in 80% yield). The molar ratio of product (Compound IV) to starting alcohol (Compound S-II) was 99.6:0.4 as determined by HPLC.

The (S)-N,N-dimethyl-(3-(1-naphthyloxy)-3-thien-2-yl) propylamine oxalic acid salt (2.0 kg, 1.15 kg dry mass equivalent, 2.9 moles) was then suspended in water (5 L) and toluene (4 L) and sodium hydroxide (50% aqueous solution, 600 g, 7.5 moles, 2.6 eq) was then added. The mixture was then stirred vigorously and the layers were separated. The aqueous layer was extracted with toluene (3 L), and the organic layers were combined, washed with water (2×2.5 L), dried with sodium sulphate (300 g) and filtered. The mixture was then evaporated to a final volume of about 4.5 L, and diisopropylethylamine (37 g, 0.29 moles, 0.1 eq.) was added followed by the addition of 1-chloroethyl chloroformate (456 g, 3.2 moles, 1.1 eq.) over 20 minutes at a temperature of between 20 and 30° C. The mixture was heated to 50° C. for 5 hours, cooled to 30° C., and washed with 10% aqueous sodium hydroxide (1 L) followed by water (1 L). Methanol (5 L) was added, and the mixture stirred at 30° C. for 44 hours. The methanol was then distilled under vacuum at a temperature of 30° C., and acetone (5 L) was added to the residue causing precipitation. The mixture was next stirred at 20° C. for 17 hours, cooled to 0° C. for 90 minutes, and filtered (and the filter cake washed with acetone (2×1 L)). The resulting solid was dried under vacuum at 40° C. to yield 535 g of duloxetine hydrochloride as an off-white solid, (1.602 moles, 99.0% ee; Yield: 56% from the oxalate intermediate, 45% from (S)-3-dimethylamino-1-(2-thienyl)-1-propanol).

Example 6

Preparation of (S)-N-methyl-(3-(1-naphthyloxy)-3-thien-2-yl) propylamine hydrochloride (Duloxetine hydrochloride)

Sodium hydroxide (0.324 kg, 8.1 moles, 2 eq), potassium carbonate (1.26 kg, 9.1 moles, 2.25 eq.) and (S)-3-dimethylamino-1-(2-thienyl)-1-propanol (750 g, 4.05 moles), were heated in DMSO (7.5 L) at 80° C. for 3 hours and cooled to 40° C. 1-fluoronaphthalene (770 g, 5.3 mol, 1.3 eq) was then added over 5 minutes. Next, the mixture was heated at 40° C. for 17 hours and then at 50-60° C. for 40 hours. The molar ratio of product (Compound IV) to starting alcohol (Compound S-II) was 85.3:14.7, and Compound IV was 92% ee as determined by HPLC of an aliquot. The mixture was then cooled to 20° C. and quenched with water (5 L). The mixture was divided in two and each portion was extracted twice with isopropyl acetate (2×2 L). The four organic phases were combined, washed with water (5 L), and pyridine sulphur trioxide complex (110 g, 0.69 moles, 0.17 eq.) was added. The mixture was then stirred at 20° C. for 30 minutes, and washed with water (5 L). Oxalic acid dihydrate (0.38 kg, 3.0 moles, 0.75 eq.) was then added, and the mixture stirred at 15-20° C. for 16 hours. The mixture was then filtered and slurried in acetone (2.5 L) and isopropyl acetate (5 L) for one hour, and then filtered to yield 2.1 kg (wet product) of (S)-N, N-dimethyl-(3-(1-naphthyloxy)-3-thien-2-yl)propylamine oxalic acid salt as an off-white solid (Yield: 75%; equivalent to 1.21 kg, (dry product)). The molar ratio of product (Compound IV) to starting alcohol (Compound S-II) was 98.7:1.3 as determined by HPLC. Compound IV oxalate salt was 92% ee as determined by chiral HPLC.

The (S)-N,N-dimethyl-(3-(1-naphthyloxy)-3-thien-2-yl) propylamine oxalic acid salt (2.0 kg, 1.16 kg dry mass equivalent, 2.9 moles) was then suspended in water (7.5 L), and sodium hydroxide (50% aqueous solution, 600 g, 7.5 moles, 2.6 eq.) was added with stirring at 20-25° C. The mixture was extracted twice with toluene (5+3 L) and the organic layers were combined, washed with water (2×2.5 L) filtered and concentrated to dryness to yield 859 g of the amine as an oil. 850 g of the oil was then dissolved in toluene (5 L) and diisopropylethylamine (79 g, 0.6 moles, 0.22 eq.) was added, followed by 1-chloroethyl chloroformate (247 g, 1.7 moles, 0.6 eq.) over 30 minutes at a temperature of 20° C. The mixture was next heated to 50° C. for 90 minutes, cooled to 36° C. and an additional 165 g of 1-chloroethyl chloroformate (1.2 moles, 0.4 eq.) was added over 15 minutes. The mixture was then heated to 50° C. for 30 minutes, cooled to 25° C., and washed with 10% aqueous sodium hydroxide (2 L). Methanol (5 L) was then added, and the mixture stirred at 25° C. for 16 hours and then at 30° C. for 24 hours. The methanol was distilled under vacuum at a temperature of 30° C., and acetone (5 L) added to the residue causing precipitation. The mixture was then stirred at 20° C. for 2 days, filtered, and the filter cake was washed with acetone (3×0.5 L). The solid was then dried under vacuum at 40° C. to yield 371 g of (S)-duloxetine hydrochloride as an off-white solid (1.111 moles, 99.3% ee; Yield: 39% from the oxalate intermediate, 29% from (S)-3-dimethylamino-1-(2-thienyl)-1-propanol).

Example 7

Preparation of (S)-N,N-dimethyl-(3-(1-naphthyloxy)-3-thien-2 yl)propylamine oxalic acid salt Sodium hydroxide (8.635 g, 216 mmol, 2 eq), potassium carbonate (33.565 g, 243 mmol, 2.25 eq.) and (S)-3-dimethylamino-1-(2-thienyl)-1-propanol (20 g, 108 mmol), were heated in DMSO (200 mL) at 80° C. (temperature inside flask) under vacuum such that approximately 100 mL of DMSO were distilled in 1 hour. An additional 100 mL of DMSO were then added, and the mixture heated at 80° C. for a further 2 hours. Thereafter, the mixture was cooled to 40° C. and stirred under an atmosphere of nitrogen. 1-Fluoronaphthalene (17.35 g, 119 mmol, 1.1 eq) was then added, and the mixture maintained with stirring at 40° C. Samples were taken periodically and analyzed by NMR. Once an approximately 92% conversion had been achieved (~24 hours), as determined by the ratio of Compounds IV and S-II in the $^1$H-NMR spectrum, the mixture was cooled to 25° C., quenched with water (150 mL) and extracted twice with isopropyl acetate (2×100 mL). The two organic phases were combined, washed with water (75 mL), and pyridine sulphur trioxide complex (1.72 g, 10.8 mmol, 0.1 eq.) was added. The mixture was then stirred at 20° C. for 60 minutes and washed with water (150 mL). The aqueous layer was analyzed to be pH 6.8. Oxalic acid dihydrate (10.9 g, 86 mmol, 0.8 eq.) was then added, and the mixture stirred at 15-20° C. for 16 hours. The mixture was then filtered and homogenized to yield 41.83 g of (S)-N,N-dimethyl-(3-(1-naphthyloxy)-3-thien-2 yl)propylamine oxalic acid salt as an off-white solid (Loss on drying: 6.94%, Titration: 98.1%, Karl Fischer: 0.06%).

Example 8

Preparation of (S)-N,N-dimethyl-(3-(1-naphthyloxy)-3-thien-2 yl)propylamine oxalic acid salt Sodium hydroxide (34.2 kg), potassium carbonate (133 kg) and (S)-3-dimethylamino-1-(2-thienyl)-1-propanol (80 kg), were heated in DMSO (1328 kg) at 70-80° C. for one hour and then distilled under vacuum at this temperature such that approximately 445 kg of DMSO were distilled within 4 hours. After this time the mixture was cooled to 40-45° C. and stirred under an atmosphere of nitrogen. 1-Fluoronaphthalene (69 kg) was then added, and the mixture maintained with stirring at 40° C. Samples were taken periodically and analyzed by HPLC. Once approximately 92% conversion had been achieved (24 hours), the mixture was cooled to 25° C., quenched with water (533 kg) and extracted twice with isopropyl acetate (2×460 kg). The two organic phases were combined, washed with water (400 kg), and added to pyridine sulphur trioxide complex (6.8 kg.). The mixture was then stirred at 20-25° C. for 30 minutes and then a solution made from ammonium chloride (32 kg) in water (533 kg) was added and the mixture stirred for 30 minutes. The aqueous layer was adjusted to pH 6.5-pH 7.0, the mixture stirred for an additional 30 minutes before the aqueous phases were separated. Oxalic acid dihydrate (44 kg) was dissolved in methanol (173 kg), and this solution was added over a period of 2 hours to the organic mixture above maintained at 40-45° C. The mixture was placed under vacuum at this temperature and 500 kg of solvent removed by distillation. Isopropyl acetate (1000 kg) was added and a further 500 kg removed by distillation under vacuum. At this point precipitation occurred, and the mixture was cooled to 0-5° C. and stirred for 2 hours. The product was filtered in a centrifuge filter, washed with isopropyl acetate (40 kg) and homogenized to give 161.93 kg of the moist product as an off-white solid (Loss on drying: 16.35%, Titration: 97.45%, Chiral assay (HPLC): 96% (S), 4% (R)-enantiomer, HPLC: oxalic acid 1.65%, 4-(3-Dimethylamino-1-thiophen-2-yl-propyl)-naphthalen-1-ol 0.005%, 1-naphthol 0.02%, N,N-dimethyl-(3-(1-naphthyloxy)-3-thien-2 yl)propylamine 98.09%).

Example 9

Preparation of (S)-N-methyl-(3-(1-naphthyloxy)-3-thien-2-yl) propylamine hydrochloride (Duloxetine hydrochloride) acetone solvate (S)-N,N-Dimethyl-(3-(1-naphthyloxy)-3-thien-2 yl)propylamine oxalic acid salt, (161.93 kg humid from the procedure above containing 4% of (R)-enantiomer, 132.78 kg dry mass equivalent), was suspended in 608 kg of deionised water and 882 kg of toluene. The mixture was stirred for 30 minutes before 61.4 kg of 50% sodium hydroxide aqueous solution was added at a rate such that the temperature did not exceed 40° C. The temperature was adjusted to 20-25° C. and the layers separated. The aqueous layer was extracted with toluene (547 kg), and the organic phases were combined and washed with deionised water (301 kg). The mixture was heated and distilled to remove 547 kg of solvent and then cooled to 20-25° C. Diisopropylethylamine (4.25 kg) was added over 30 minutes and without allowing the temperature to increase above 30° C., then 56.7 kg of 1-chloroethyl chloroformate was added. The mixture was heated to 50±3° C. and stirred for 2 hours at this temperature. It was then cooled to 20-25° C. and washed first with a mixture made from 85 kg of water and 47.3 kg of 30% aqueous ammonium hydroxide and then water 67 kg. To the organic layer, 519 kg of methanol was added, and the mixture stirred at 30-40° C. for not less than 24 hours. The mixture was filtered and distilled under vacuum to remove 823 kg of solvent without the internal temperature going above 40° C. Filtered acetone (518 kg) was added, and the mixture stirred at 20-25° C. for 2 hours. The mixture was cooled to 0-5° C., stirred for 2 hours and then filtered in a centrifuge filter, washing the product with 2×15 kg of acetone to yield 108.32 kg of duloxetine hydrochloride acetone solvate (Loss on drying 26.89%; Assay (titration) 99.62%; Karl Fischer analysis 0.00% water; analysis: 99.75% by HPLC peak area at 220 nm, impurities 1-naphthol 0.01%, 4-(3-Methylamino-1-thiophen-2-yl-propyl)-naphthalen-1-ol 0.01%, N,N-dimethyl-3-(1-naphthaleneyloxy)-3-(2-thienyl)-1-propylamine. 0.01%; Chiral assay: 99.2% (S)-duloxetine hydrochloride, 0.8% (R)-duloxetine hydrochloride).

Example 10

Figure 2:
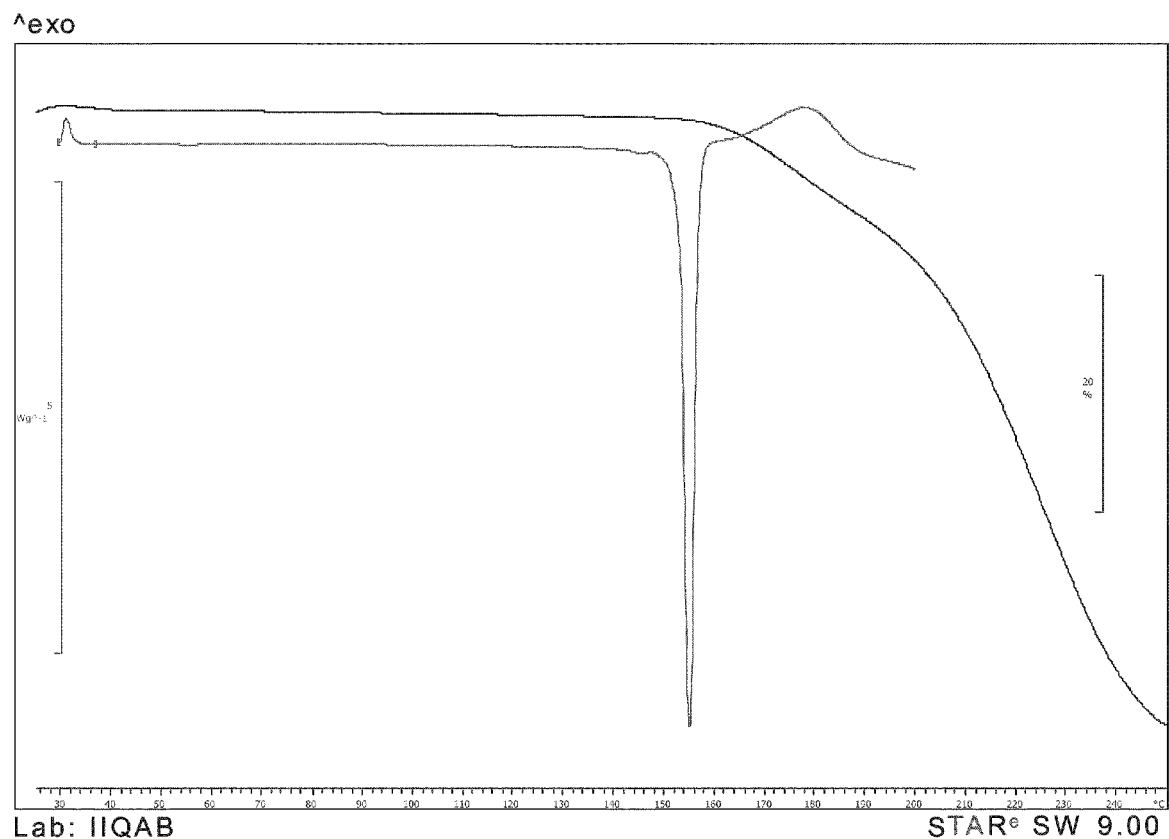
FIG. 2 illustrates the combined Differential Scanning Calorimetry (DSC) and Thermogravimetric Analysis (TGA) thermogram of (S)-N,N-dimethyl-(3-(1-naphthyloxy)-3-thien-2-yl)propylamine oxalic acid salt, Form A, obtained in Example 10.
Figure 3:
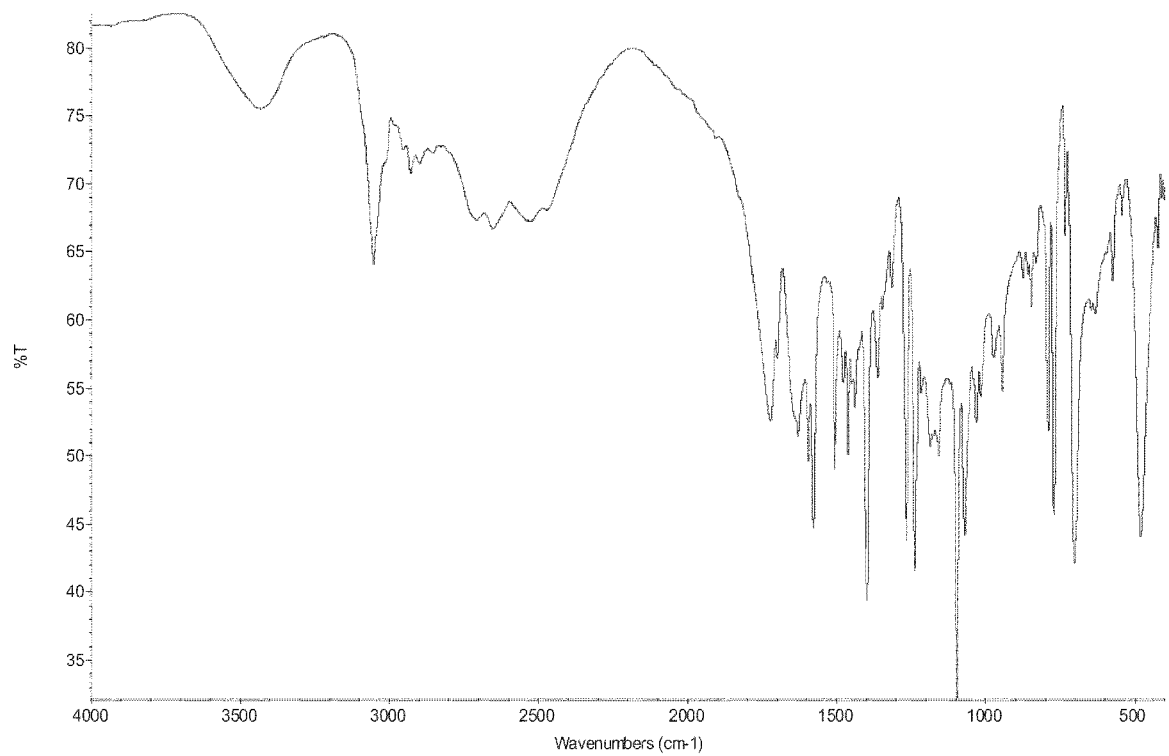
FIG. 3 illustrates the IR spectra of (S)-N,N-dimethyl-(3-(1-naphthyloxy)-3-thien-2-yl)propylamine oxalic acid salt, Form A, obtained in Example 11.

Preparation of (S)-N,N-dimethyl-(3-(1-naphthyloxy)-3-thien-2-yl)propylamine oxalic acid salt (S)-N,N-dimethyl-(3-(1-naphthyloxy)-3-thien-2 yl)propylamine (10 g, 32.1 mmoles) was dissolved in isopropyl acetate (50 mL) at ambient temperature. A solution of oxalic acid dihydrate (3.64 g, 25.7 moles, 0.8 eq) in water (30 mL) was then added. The resulting mixture was stirred for 21 hours and filtered. The filter cake was washed with isopropyl acetate (10 mL) and dried under vacuum at 40° C. to yield 10.87 g of the product as a white solid (Yield: 84.2%; HPLC (peak area at 220 nm) oxalic acid 1.78%, 4-[3-dimethylamino-1-(2-thienyl)-1-propyl]naphthol 0.10%, 1-naphthol 0.35%, (S)-N,N-dimethyl-(3-(1-naphthyloxy)-3-thien-2-yl) propylamine 97.65%; Titration: 99.5%; Karl Fischer: 0.06%; XRD as shown in FIG. 1 (Form A); IR essentially as shown in FIG. 3 (Form A); TGA DSC as shown in FIG. 2, mp onset 152.6° C.).

Example 11

Preparation of (S)-N,N-dimethyl-(3-(1-naphthyloxy)-3-thien-2-yl)propylamine oxalic acid salt (S)-N,N-dimethyl-(3-(1-naphthyloxy)-3-thien-2 yl)propylamine (10 g, 32.1 mmoles) was dissolved in isopropyl acetate (50 mL) at ambient temperature. A solution of oxalic acid dihydrate (3.64 g, 25.7 mmoles, 0.8 eq) in methanol (4 mL) was then added. An additional volume of isopropyl acetate (50 mL) was added for improved stirring. The resulting mixture was stirred for 16 hours and filtered. The filter cake was washed with isopropyl acetate (10 mL) and dried under vacuum at 55° C. to yield 10.21 g of the product as a white solid (Yield: 78.9%; HPLC (peak area at 220 nm) oxalic acid 1.66%, 4-[3-dimethylamino-1-(2-thienyl)-1-propyl]naphthol not detected, 1-naphthol not detected, (S)-N,N- dimethyl-(3-(1-naphthyloxy)-3-thien-2-yl)propylamine 98.24%; Titration: 100.1%; Karl Fischer: 0.22%; XRD as shown in FIG. 1 (Form A); IR as shown in FIG. 3 (Form A).

Example 12

Preparation of (S)-N,N-dimethyl-(3-(1-naphthyloxy)-3-thien-2-yl)propylamine oxalic acid salt (S)-N,N-dimethyl-(3-(1-naphthyloxy)-3-thien-2 yl)propylamine (10 g, 32.1 mmoles) was dissolved in isopropyl acetate (50 mL) at ambient temperature. A solution of oxalic acid dihydrate (3.64 g, 25.7 mmoles, 0.8 eq) in isopropanol (30 mL) was then added dropwise. The resulting mixture was stirred for 2 hours and filtered. The filter cake was dried under vacuum at 50° C. to yield 10.14 g of the product as a white solid (Yield: 78.6%; HPLC (peak area at 220 nm) oxalic acid 1.56%, 4-[3-dimethylamino-1-(2-thienyl)-1-propyl]naphthol not detected, 1-naphthol not detected, (S)-N,N-dimethyl-(3-(1-naphthyloxy)-3-thien-2-yl)propylamine 98.36%; Titration: 99.4%; Karl Fischer: 0.06%; IR essentially as shown in FIG. 3, Form A).

Example 13

Figure 4:
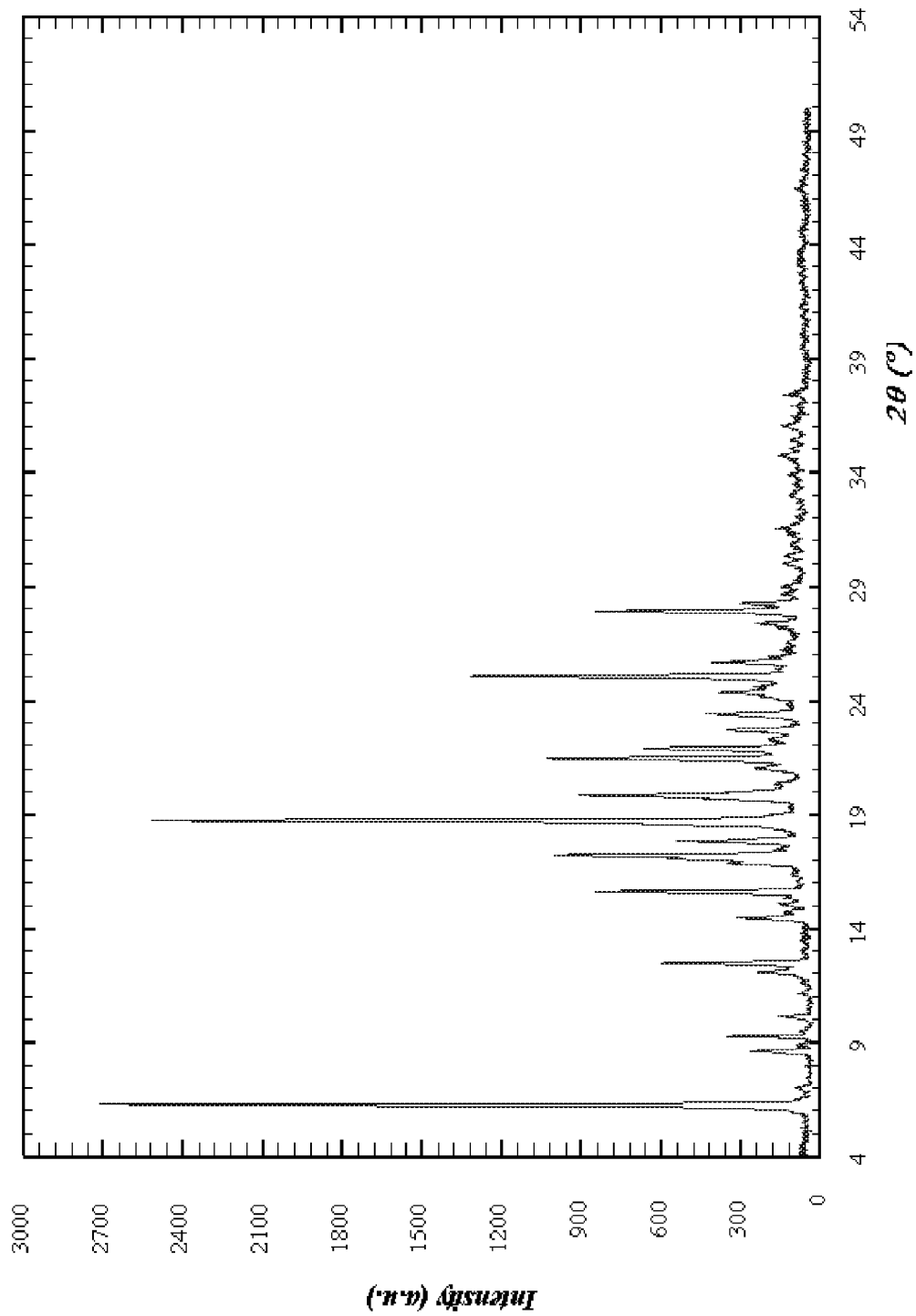
FIG. 4 illustrates the X-ray powder diffractogram (XRD) of (S)-N,N-dimethyl-(3-(1-naphthyloxy)-3-thien-2-yl)propylamine oxalic acid salt, Form C, obtained in Example 13.
Figure 5:
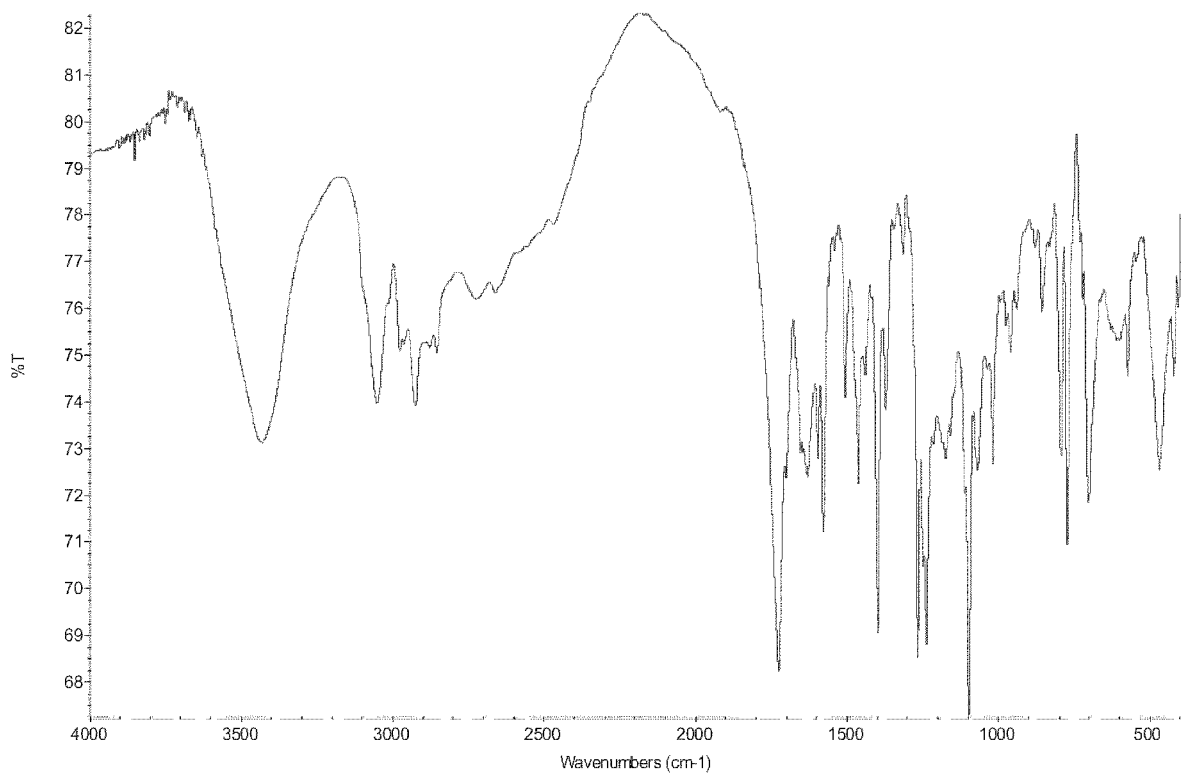
FIG. 5 illustrates the IR spectra of (S)-N,N-dimethyl-(3-(1-naphthyloxy)-3-thien-2-yl)propylamine oxalic acid salt, Form C, obtained in Example 13.

Preparation of (S)-N,N-dimethyl-(3-(1-naphthyloxy)-3-thien-2-yl)propylamine oxalic acid salt (S)-3-dimethylamino-1-(2-thienyl)-1-propanol (20 g, 108 mmoles), potassium hydroxide (12.11 g, 216 mmoles) and DMSO (300 mL) were charged in a reactor. The suspension was heated to 75-80° C. and 100 mL of solvent distilled under vacuum in 1 hour. The mixture then was allowed to cool to 40° C. under nitrogen and 1-fluoronaphthalene (15.3 mL, 119 mmoles) was added. The mixture was stirred at 40° C. for 46 hours. The mixture was allowed to cool to ambient temperature. Water (300 mL) and isopropyl acetate (200 mL) were added; the mixture was stirred and the layers were separated. The aqueous layer was extracted with isopropyl acetate (100 mL). The organic layers were combined and washed with water (100 mL). To this solution pyridine sulfur trioxide complex (1.7 g, 11 mmoles) was added and the mixture stirred at room temperature for 1 hour. The mixture was washed with water (50 mL). The aqueous pH was 6.5. To the organic layer was added oxalic acid dihydrate (10.9 g, 86 mmoles). The mixture was stirred for 1 hour at ambient temperature and then filtered. The filter cake was washed with isopropyl acetate (25 mL) and dried under vacuum at 50° C. to yield 28.96 g of the product as a white solid (Yield: 67%; Titration 89.68%; HPLC (peak area at 220 nm) oxalic acid 2.09%, 4-[3-dimethylamino-1-(2-thienyl)-1-propyl]naphthol 0.045%, 1-naphthol 0.20%, (S)-N,N-dimethyl-(3-(1-naphthyloxy)-3-thien-2-yl)propylamine 95.19%; XRD analysis as shown in FIG. 4, Form C; IR as shown in FIG. 5, Form C).

Example 14

Figure 6:
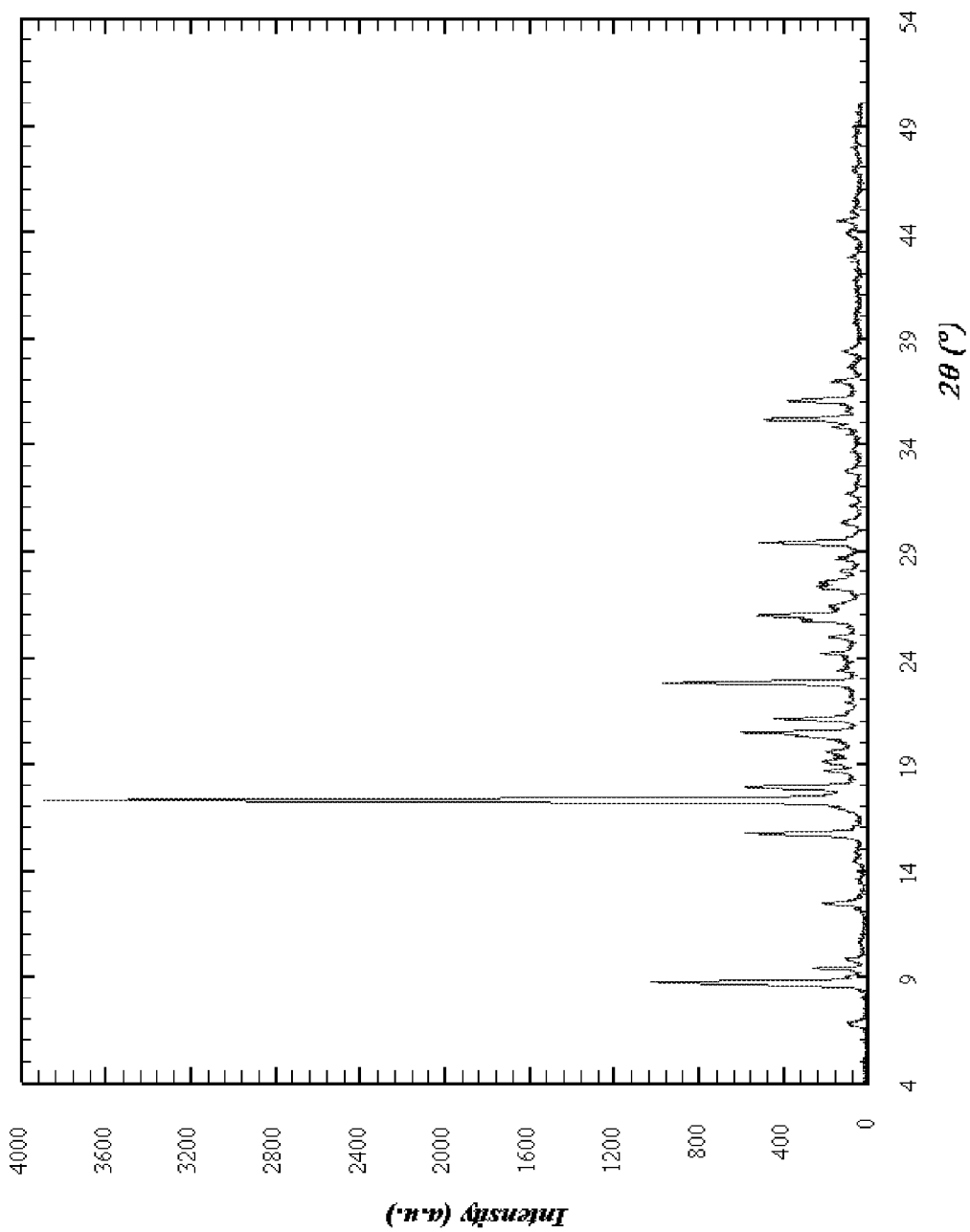
FIG. 6 illustrates the X-ray powder diffractogram (XRD) of (S)-N,N-dimethyl-(3-(1-naphthyloxy)-3-thien-2-yl)propylamine oxalic acid salt, Form B, obtained in Example 14.
Figure 7:
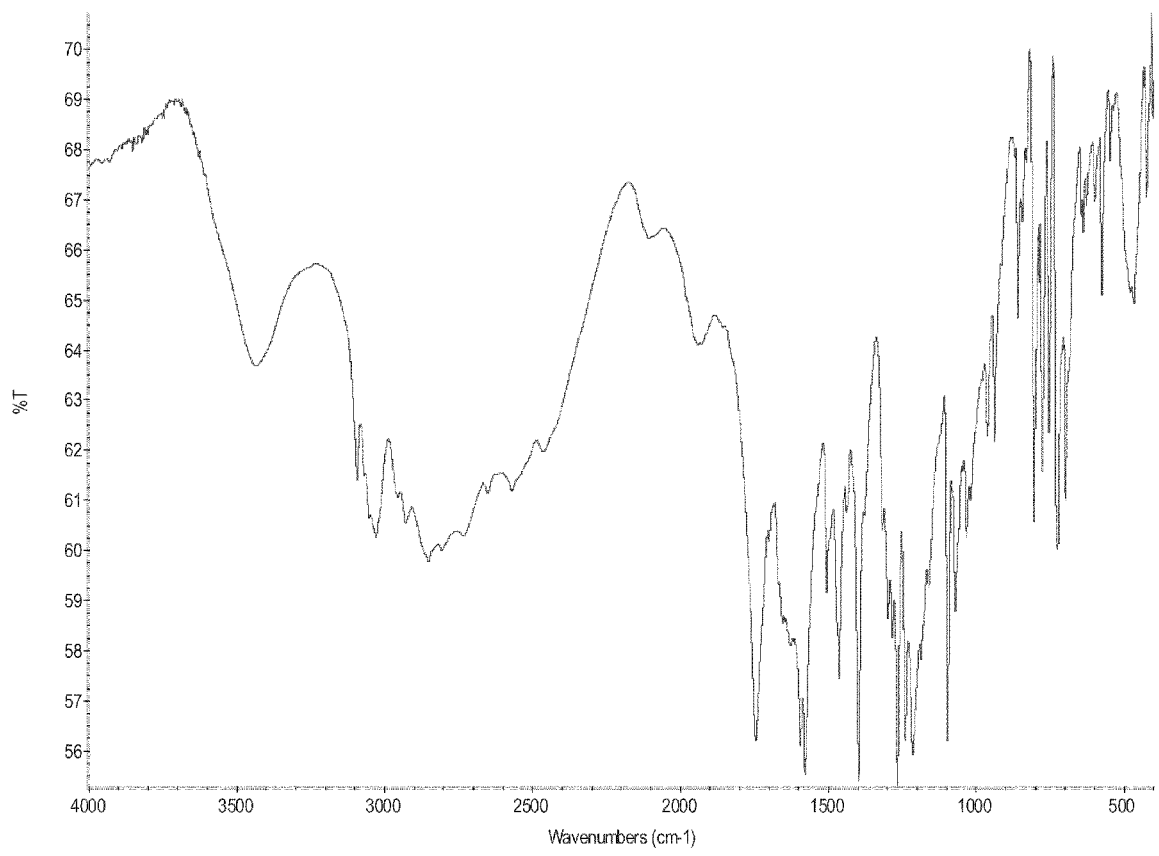
FIG. 7 illustrates the IR spectra of (S)-N,N-dimethyl-(3-(1-naphthyloxy)-3-thien-2-yl)propylamine oxalic acid salt, Form B, obtained in Example 14.

Preparation of (S)-N,N-dimethyl-(3-(1-naphthyloxy)-3-thien-2-yl)propylamine oxalic acid salt (S)-3-dimethylamino-1-(2-thienyl)-1-propanol (50 g, 269.8 mmoles), sodium hydroxide (21.58 g, 539.7 mmoles), potassium carbonate (83.91 g, 607.2 mmoles) and 1-methyl-2-pyrrolidinone (500 mL) were charged in a reactor. The suspension was heated to 80° C. and 10 mL of solvent distilled under vacuum in 4 hours. The mixture then was allowed to cool to 40° C. under argon and 1-fluoronaphthalene (38 mL, 296.8 mmoles) was added. The mixture was stirred at 40° C. for 40 hours, and then at 60° C. for 24 hours. The mixture was allowed to cool to ambient temperature. Water (350 mL) and isopropyl acetate (150 mL) were added; the mixture was stirred and the layers were separated. The aqueous layer was extracted with isopropyl acetate (130 mL). The organic layers were combined and washed with water (250 mL). To this solution pyridine sulfur trioxide complex (4.3 g, 27.0 mmoles) was added and the mixture stirred at room temperature for 1 hour. The mixture was washed with water (300 mL). The aqueous pH was 6. To the organic layer was added oxalic acid dihydrate (27.2 g, 215.8 moles). The mixture was stirred for 20 hours at ambient temperature and then filtered. The filter cake was washed with isopropyl acetate (2×40 mL) and dried under vacuum at 50° C. to yield 57.39 g of the product as a white solid (Yield: 53%; HPLC (peak area at 220 nm) oxalic acid 2.69%, 4-[3-dimethylamino-1-(2-thienyl)-1-propyl]naphthol 0.21%, 1-naphthol 0.43%, (S)-N,N-dimethyl-(3-(1-naphthyloxy)-3-thien-2-yl)propylamine 95.42%; XRD analysis as shown in FIG. 6, Form B; IR as shown in FIG. 7, Form B; Titration 93.14%).

Example 15

Figure 8:
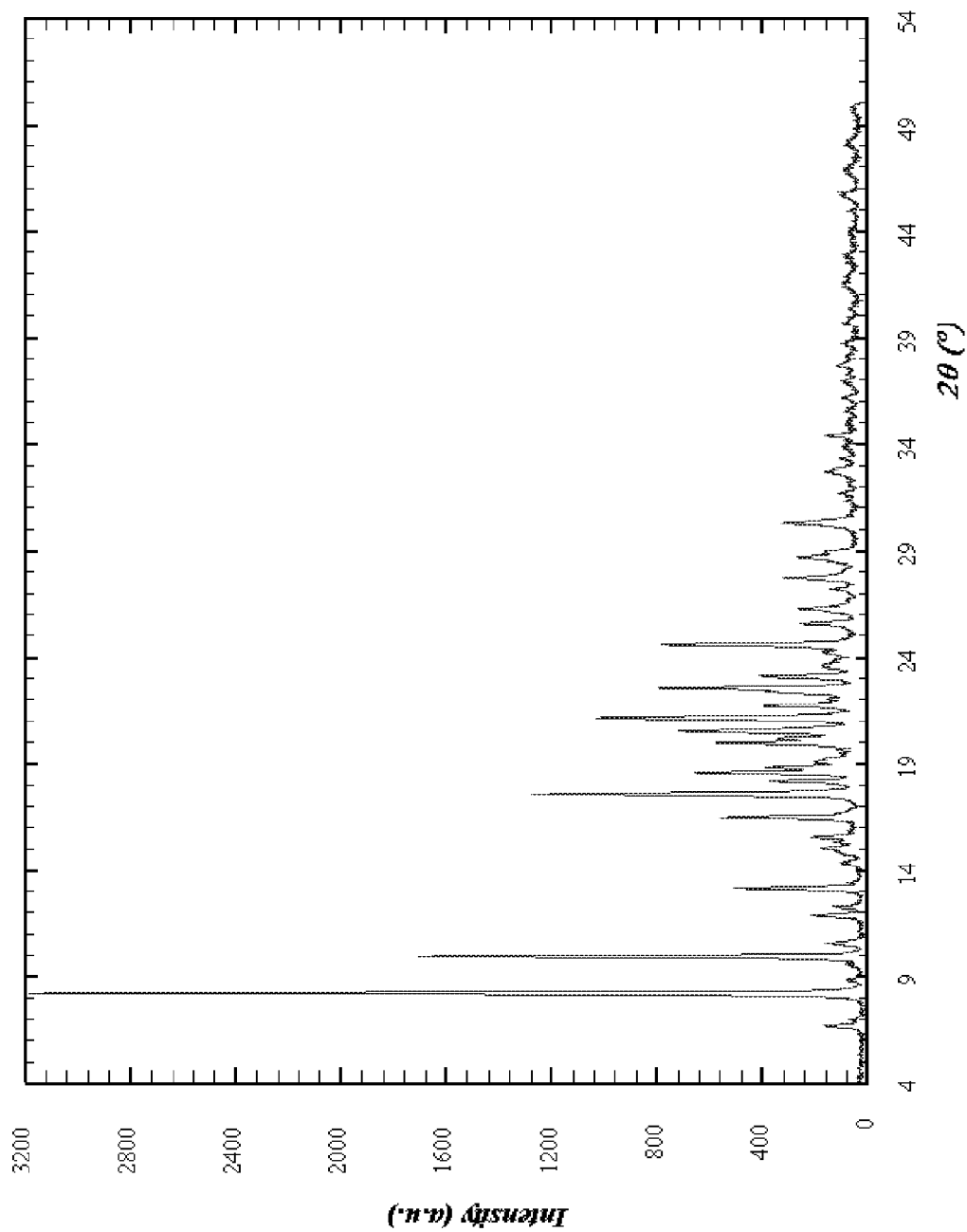
FIG. 8 illustrates the X-ray powder diffractogram (XRD) of (S)-N,N-dimethyl-(3-(1-naphthyloxy)-3-thien-2-yl)propylamine oxalic acid salt, Form E, obtained in Example 15.
Figure 9:
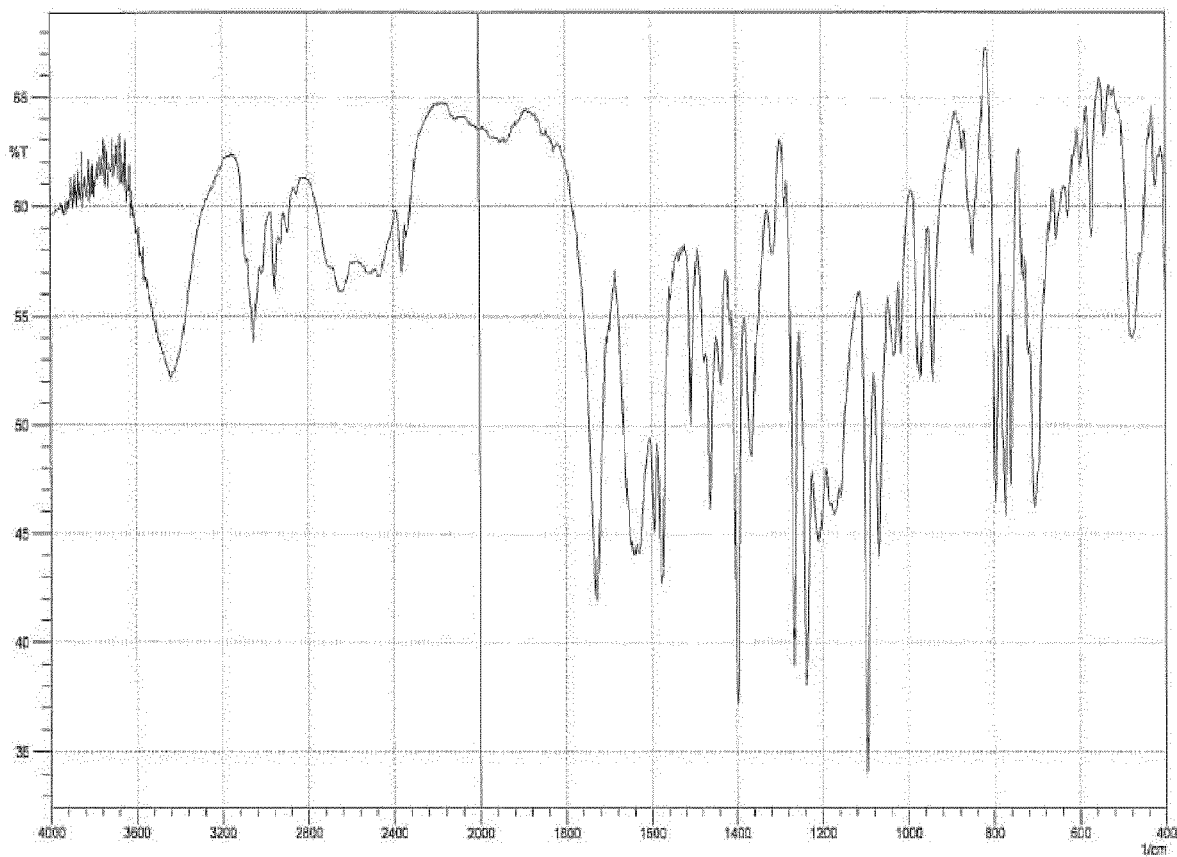
FIG. 9 illustrates the IR spectra of (S)-N,N-dimethyl-(3-(1-naphthyloxy)-3-thien-2-yl)propylamine oxalic acid salt, Form E, obtained in Example 15.

Preparation of (S)-N,N-dimethyl-(3-(1-naphthyloxy)-3-thien-2-yl)propylamine oxalic acid salt Sodium hydroxide (34.2 kg), potassium carbonate (133 kg) and (S)-3-dimethylamino-1-(2-thienyl)-1-propanol (80 kg), were heated in DMSO (1328 kg) at 70-80° C. for one hour and then distilled under vacuum at this temperature such that approximately 445 kg of DMSO were distilled within 4 hours. After this time the mixture was cooled to 40-45° C. and stirred under an atmosphere of nitrogen. 1-Fluoronaphthalene (69 kg) was then added and the mixture maintained with stirring at 40° C. Samples were taken periodically and analyzed by HPLC. Once approximately 92% conversion had been achieved (24 hours), the mixture was cooled to 25° C., quenched with water (533 kg) and extracted twice with isopropyl acetate (2×460 kg). The two organic phases were combined, washed with water (400 kg), and added to pyridine sulphur trioxide complex (6.8 kg.). The mixture was then stirred at 20-25° C. for 30 minutes and then a solution made from ammonium chloride (32 kg) in water (533 kg) was added and the mixture stirred for 30 minutes. The aqueous layer was adjusted to pH 6.5-pH 7.0, the mixture stirred for an additional 30 minutes before the aqueous phases were separated. Oxalic acid dihydrate (44 kg) was dissolved in methanol (173 kg.) and this solution was added over a period of 2 hours to the organic mixture above maintained at 40-45° C. The mixture was placed under vacuum at this temperature and 500 kg of solvent removed by distillation. Isopropyl Acetate (1000 kg) was added and a further 500 kg removed by distillation under vacuum. At this point precipitation occurred and the mixture was cooled to 0-5° C. and stirred for 2 hours. The product was filtered in a centrifuge filter, washed with isopropyl acetate (40 kg) and homogenized to yield 161.93 kg of the moist product as an off-white solid (Loss on Drying: 16.35%; Titration: 97.45%; Chiral Assay: 96% (S), 4% (R)-enantiomer; HPLC: oxalic acid 1.65%, 4-[3-dimethylamino-1-(2-thienyl)-1-propyl]naphthol 0.005%, 1-naphthol 0.02%, N,N-dimethyl-(3-(1-naphthyloxy)-3-thien-2 yl)propylamine 98.09%; XRD as shown in FIG. 8, Form E; IR as shown FIG. 9, Form E).

What is claimed is:

1. A process for preparing duloxetine hydrochloride comprising (i) reacting (S)-3-(dimethylamino)-1-(2-thienyl)-1-propanol (Compound S-II) and 1-fluoronaphthalene (Compound III) and at least one alkaline metal hydroxide or alkoxide in DMSO or DMSO-cosolvent mixtures so as to form (S)-N,N-dimethyl-3-(1-naphthalenyloxy)-3-(2-thienyl)-1-propylamine (Compound IV), wherein the process does not require the use of a phase transfer catalyst, (ii) converting Compound IV to a carbamate form via treatment with a formate, and (iii) converting the resulting carbamate form of Compound IV to its hydrochloride salt, thereby preparing duloxetine hydrochloride.

2. The process of claim 1 further comprising the use of potassium carbonate or sodium sulphate.

3. The process of claim 1, wherein the at least one alkaline metal hydroxide or alkoxide is at least one of NaOH, KOH, CsOH, sodium tert-butoxide, sodium tertpentoxide, and potassium tertpentoxide.

4. The process of claim 1, further comprising at least partially distilling the DMSO or DMSO-cosolvent such that water is removed and the rate of the reaction increases.

5. The process of claim 1, wherein step (ii) comprises reacting Compound IV with 1-chloroethyl chloroformate in the presence of an acid scavenger in a solvent, thereby obtaining (S)—N-methyl-[3-(naphthalen-1-yloxy)-3-thiophen-2-yl-propyl]-carbamic acid 1-chloroethyl ester as the carbamate form.

6. The process of claim 5, wherein the amount of the acid scavenger is approximately 0.02 to approximately 2 equivalents relative to Compound IV.

7. The process of claim 5, wherein the amount of the acid scavenger is approximately 0.05 to approximately 1 equivalents relative to Compound IV.

8. The process of claim 5, wherein the amount of acid scavenger is approximately 0.1 equivalents relative to Compound IV.

9. The process of claim 5, wherein the acid scavenger hindered is diisopropylethylamine.

10. The process of claim 5, wherein the solvent is at least one of toluene, xylene, ethyl acetate, isopropyl acetate, isobutyl acetate, tertbutyl methyl ether, tetrahydrofuran, and combinations thereof.

11. The process of claim 10, wherein the solvent is at least one of toluene, xylene, and combinations thereof.

12. The process of claim 10, wherein the solvent is at least one of ethyl acetate, isopropyl acetate, isobutyl acetate, and combinations thereof.

13. The process of claim 10, wherein the solvent is at least one of tertbutyl methyl ether, tetrahydrofuran, and combinations thereof.

14. The process of claim 5, wherein step (iii) comprises a treatment step with an alcohol at a temperature of less than or equal to about 50° C.

15. The process of claim 5, wherein step (iii) comprises a treatment step with an alcohol at a temperature of less than or equal to about 40° C.

16. The process of claim 14, wherein the alcohol is methanol.

17. The process of claim 15, wherein the alcohol is methanol.

* * * * *